United States Patent
Thompson

(10) Patent No.: US 10,267,872 B2
(45) Date of Patent: Apr. 23, 2019

(54) MAGNETIC FLUX PROBE DATA STREAMER FOR A GENERATOR

(71) Applicant: Siemens Energy, Inc., Orlando, FL (US)

(72) Inventor: Edward David Thompson, Casselberry, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 28 days.

(21) Appl. No.: 15/704,109

(22) Filed: Sep. 14, 2017

(65) Prior Publication Data

US 2019/0079150 A1    Mar. 14, 2019

(51) Int. Cl.
| | |
|---|---|
| *G01R 35/00* | (2006.01) |
| *G01R 33/20* | (2006.01) |
| *A61B 5/06* | (2006.01) |
| *G01R 33/02* | (2006.01) |
| *G01V 3/08* | (2006.01) |

(52) U.S. Cl.
CPC .............. *G01R 33/20* (2013.01); *A61B 5/062* (2013.01); *G01R 33/0206* (2013.01); *G01V 3/081* (2013.01); *H04Q 2209/88* (2013.01)

(58) Field of Classification Search
CPC ..................................................... G01R 33/20
See application file for complete search history.

(56) References Cited

U.S. PATENT DOCUMENTS

| | | | |
|---|---|---|---|
| 5,754,943 A * | 5/1998 | Arai ......................... | H04B 3/04 330/129 |
| 6,990,427 B2 | 1/2006 | Kirsch et al. | |
| 2015/0281808 A1 | 10/2015 | Shinchi et al. | |

* cited by examiner

*Primary Examiner* — Clayton E. LaBalle
*Assistant Examiner* — Jas A Sanghera

(57) ABSTRACT

A device for streaming magnetic flux data generated by an electrical generator for a power plant. The device includes a flux probe located on the generator to enable detection of a magnetic flux of the generator. The device also includes a computer having an interface, wherein the computer includes an analog-to-digital converter. In addition, the device includes a calibration circuit attached to the flux probe by a first cable and the interface by a second cable. The calibration circuit measures a resistance of the second cable and a voltage of the flux probe wherein ends of the second cable are shorted when measuring the cable resistance and the flux probe voltage. A gain is determined based on the cable resistance and flux probe voltage to provide a suitable input voltage at the interface to deliver the magnetic flux data to the computer.

12 Claims, 3 Drawing Sheets

MAGNETIC FLUX PROBE DATA STREAMER FOR A GENERATOR

BACKGROUND

1. Technical Field

Aspects of the present invention relate to magnetic flux data obtained by a flux probe, and more particularly, to a flux probe data streamer that includes a calibration circuit connected between the flux probe and a computer by first and second cables, respectively, wherein the calibration circuit measures a resistance of the second cable and a voltage of the flux probe to determine a gain based on the cable resistance and flux probe voltage to provide a suitable input voltage at a computer interface to deliver the magnetic flux data to the computer.

2. Description of Related Art

It is desirable for a power plant operator to monitor a magnetic flux generated by an electric generator having a rotor and a stator in order to identify an interturn short circuit in a rotor winding. In order to detect a shorted turn, a sensor, such as a known flux probe, is affixed to a stator wedge in an air gap between the rotor and stator to measure the magnetic flux.

Data from a flux probe, such as waveform data, is sent via a wire or cable to a known data acquisition system located near the generator that continuously reads and/or records the data and provides periodic analysis of the data. The data acquisition system includes components that enable signal acquisition of an analog flux probe signal. In addition, the system includes an analog-to-digital (A/D) converter to provide A/D conversion of the flux probe signal. Such systems may only log data on alarms, or not on a continuous basis without the purchase of additional expensive servers or custom hardware. The data acquisition system may also be connected to an offsite computer via a network adapter and fiber optic network that utilizes media converters in order to send data to the computer for archiving and/or analysis. But, the use of a network adapter, A/D converter, fiber optic network, media converters along with custom software for communicating with the computers increases cost and complexity.

SUMMARY

Aspects of the present invention relate to a device for streaming magnetic flux data generated by an electrical generator for a power plant. The device includes a flux probe located on the generator to enable detection of a magnetic flux of the generator. The device also includes a computer having an interface, wherein the computer includes an A/D converter. In addition, the device includes a calibration circuit attached to the flux probe by a first cable and the interface by a second cable. The calibration circuit measures a resistance of the second cable and a voltage of the flux probe wherein ends of the second cable are shorted when measuring the cable resistance. A gain is determined based on the cable resistance and flux probe voltage to provide a suitable input voltage at the interface to deliver the magnetic flux data to the computer.

In addition, a method is disclosed for streaming magnetic flux data generated by an electrical generator for a power plant. The method includes providing a flux probe located on the generator to enable detection of a magnetic flux of the generator. The method also includes providing a computer having an interface, wherein the computer includes an A/D converter. In addition, the method includes providing a calibration circuit attached to the flux probe by a first cable and the interface by a second cable. A resistance of the second cable and a voltage of the flux probe are measured via the calibration circuit. Further, a gain based on the cable resistance and flux probe voltage is determined to provide a suitable input voltage at the interface to deliver the magnetic flux data to the computer.

Those skilled in the art may apply the respective features of the present invention jointly or severally in any combination or sub-combination.

BRIEF DESCRIPTION OF DRAWINGS

The exemplary embodiments of the present invention are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
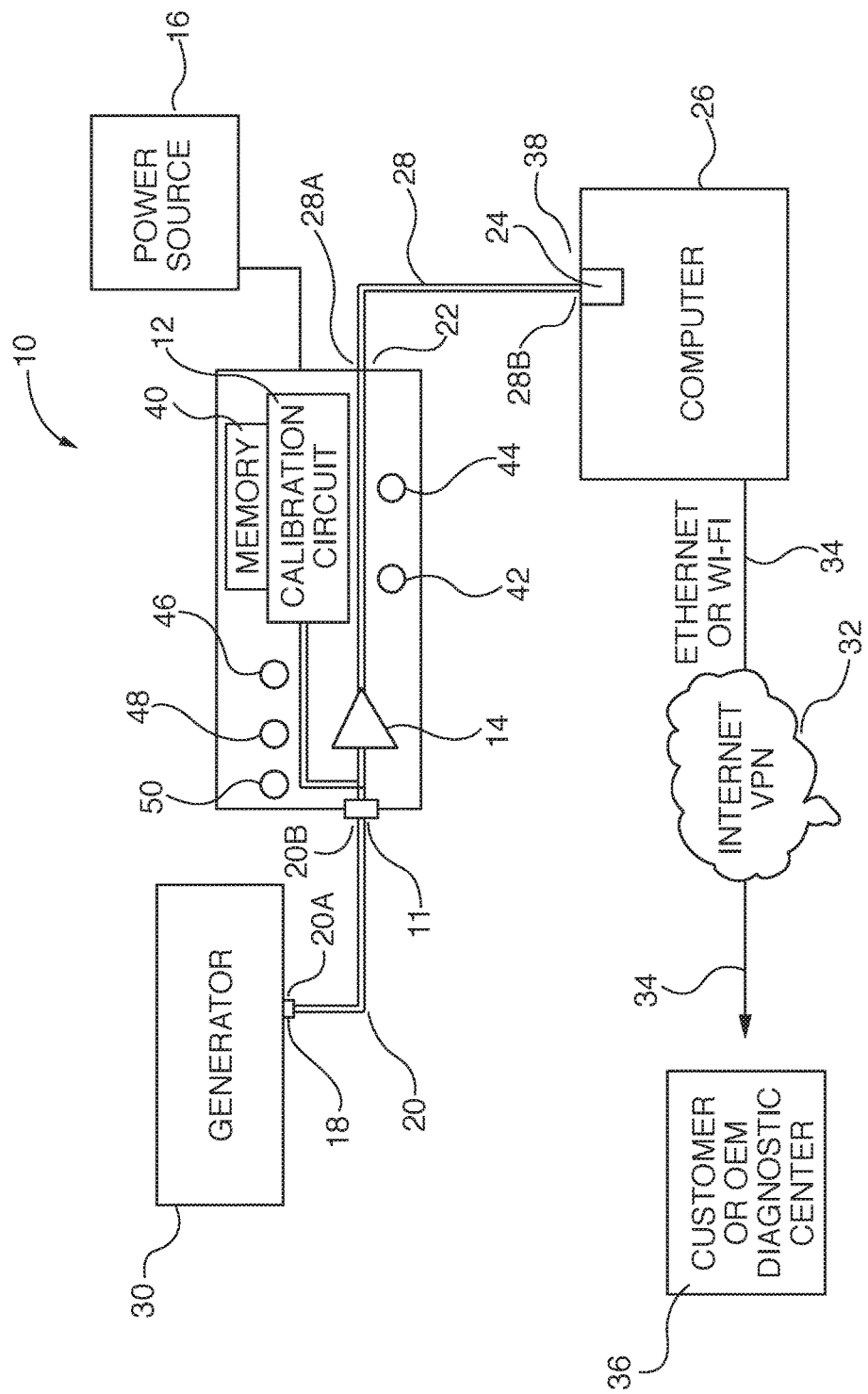
FIG. 1 depicts a streaming device for streaming magnetic sensor data, such as a flux probe data, to a computer in accordance with an aspect of the present invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Referring to FIG. 1, a streaming device 10 for streaming or transmitting magnetic sensor data, such as a flux probe data, is shown. The device 10 includes a self-configuring calibration circuit 12 having electronics that includes circuitry for measuring voltage, resistance, current and other electronic measurements, an amplifier 14 and a power source 16 such as a battery or permanent power supply for energizing the device 10. First 20A and second 20B ends of a first conductor or first cable 20, such as a known BNC or coaxial cable, may be attached to a flux probe 18 and an input 11 of the device 10, respectively. The flux probe 18 can be affixed to a stator wedge in an air gap between a rotor and stator of a generator 30 and located to enable measurement of magnetic flux. First 28A and second 28B ends of a second conductor or cable 28, for example a twisted pair or coaxial cable, may be connected to an output 22 of the device 10 and a computer interface 24 of a conventional computer 26, respectively. The interface 24 provides access to known audio codecs provided by the computer 26 that enable high quality A/D conversion that provides sufficient resolution for analyzing flux probe data. For example, the interface 24 may be a standard audio input port of the computer 26, a universal serial bus (USB) port or other suitable port of the computer 26. In accordance with an aspect of the present invention, magnetic flux waveform data detected by the flux probe 18 is input to the computer 26 via the device 10. Data can then be continuously recorded and archived using a variety of readily available free or low cost audio software, a standard sound recorder such as that available on a computer using a Microsoft Windows® operating system, or custom software if desired. Existing computer algorithms could be used to analyze the data or the computer 26 can continuously transmit the data over the Internet 32 via Ethernet or wirelessly 34 to an original equipment manufacturer (OEM) or customer diagnostic center 36 for analysis as part of a monitoring contract or program.

The output of the flux probe 18 may vary depending on the characteristics of the generator 30 that is being monitored. In order to ensure a suitable input voltage range for the computer audio input, the device 10 is calibrated. In order to perform the calibration, cable wire ends 38 of the second cable 28 terminating at the interface 24 may be first connected or shorted together via a shorting connector by power plant personnel. A calibration mode is then initiated by the power plant personnel wherein the device 10 measures flux probe voltage and the resistance of the second cable 20 length. The calibration process may be accomplished in two steps where the flux probe voltage is measured with the second cable 28 disconnected, and subsequently the second cable resistance is measured with the flux probe 18 disconnected. In an alternate embodiment, the calibration circuit 12 may allow both measurements without manual cable disconnecting by the electronics and a programming sequence making the appropriate connection for each measurement. A suitable gain can be calculated based on the flux probe voltage and the resistance of the second cables 28. The gain can be then set via the amplifier 14 to provide the proper voltage at the computer 26 (typically 5 volts maximum scale). In an embodiment of the present invention, the gain setting may be obtained by a look-up table stored in memory 40 that can be derived from testing of a prototype device using various input signals and cable lengths/wire resistances. In accordance with an aspect, the present invention extends the allowable analog cable length 28 by adjusting voltage based on known characteristics of the cabling. The calibration mode process may be accomplished by software programmed into associated calibration electronics of the calibration circuit 12.

A cable distance check may also be performed by measuring the resistance and a warning may be generated if the cable 28 is determined to be too long to provide a sufficient quality signal flux probe signal. In particular, the maximum allowable length is dependent on the individual flux probe signal and the type of cable 28 that is used. It is noted that without the device 10, an engineering study to evaluate each flux probe, generator and cable length arrangement would be required.

The device 10 includes calibrate button 42 that is activated by power plant personnel to turn on and off the calibration mode and a stream toggle button 44 to turn on and off the transmitting or streaming of waveform data detected by the flux probe 18 to the computer 26. The device 10 also includes a calibration indicator 46, such as a light emitting diode (LED) light source, to indicate that calibration is being performed and a streaming indicator 48 to indicate that streaming of waveform data is in progress.

For either temporary installations or when no house power is conveniently available, the power source 16 for the device 10 could be a readily available standard battery pack such as that typically used for rechargeable cordless drills. Such batteries are readily available in a power plant and can be replaced with a new battery when needed or on a maintenance schedule. In particular, the device 10 includes a low power indicator 50 to indicate when the battery needs to be replaced. The device 10 may also include a spring loaded connector designed to fit a variety of battery types. In addition, a standard transformer power supply may be used if an electrical outlet near the generator 30 is available.

Figure 2:
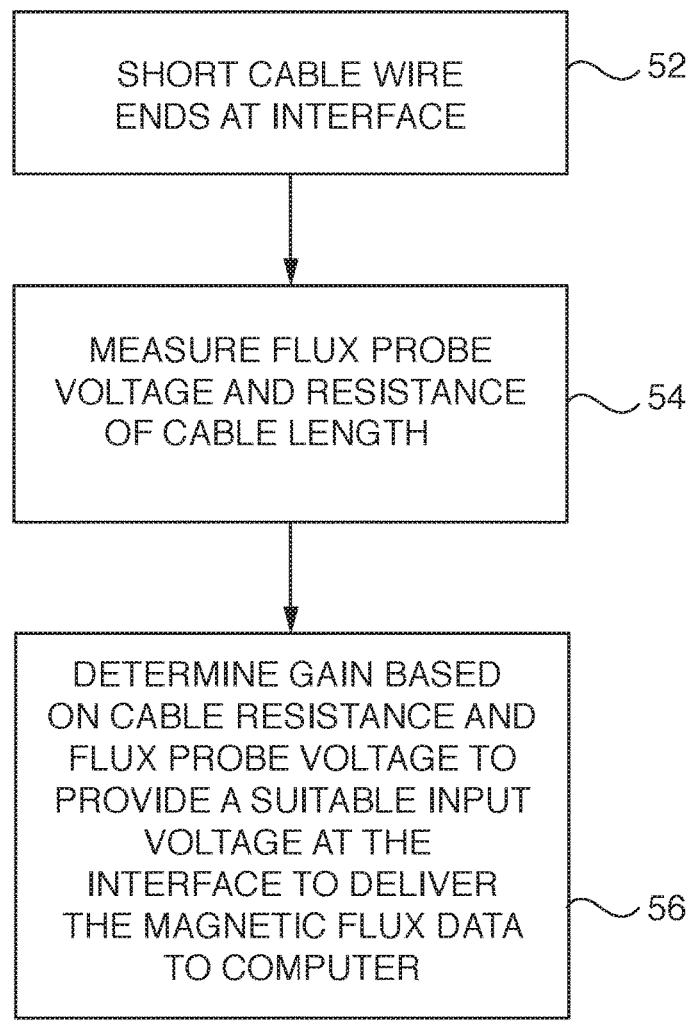
FIG. 2 depicts a process for determining an input voltage for a computer interface.

Referring to FIG. 2, a process for determining an input voltage for the interface 24 is shown. At step 52, cable wire ends 38 of the second cable 28 terminating at the interface 24 may be first connected or shorted together via a shorting connector by power plant personnel. At step 54, a flux probe voltage and the resistance of the second cable 28 length can be measured. Next, a gain can be determined based on the cable resistance and flux probe voltage to provide a suitable input voltage at the interface 24 to transmit the magnetic flux data to the computer 26 at step 56.

In accordance with an aspect, the present invention provides a device and method for data acquisition of substantially continuous flux probe data for archival purposes and/or analysis at a location other than a power plant facility such as a centrally located diagnostic center. In accordance with as aspect, the present invention eliminates the use of an A/D converter and network hardware near the generator 18 thereby reducing costs. In an embodiment of the present invention, data acquisition and archiving is provided by capabilities already built in a conventional computer 26 thereby minimizing the amount of custom software.

Figure 3:
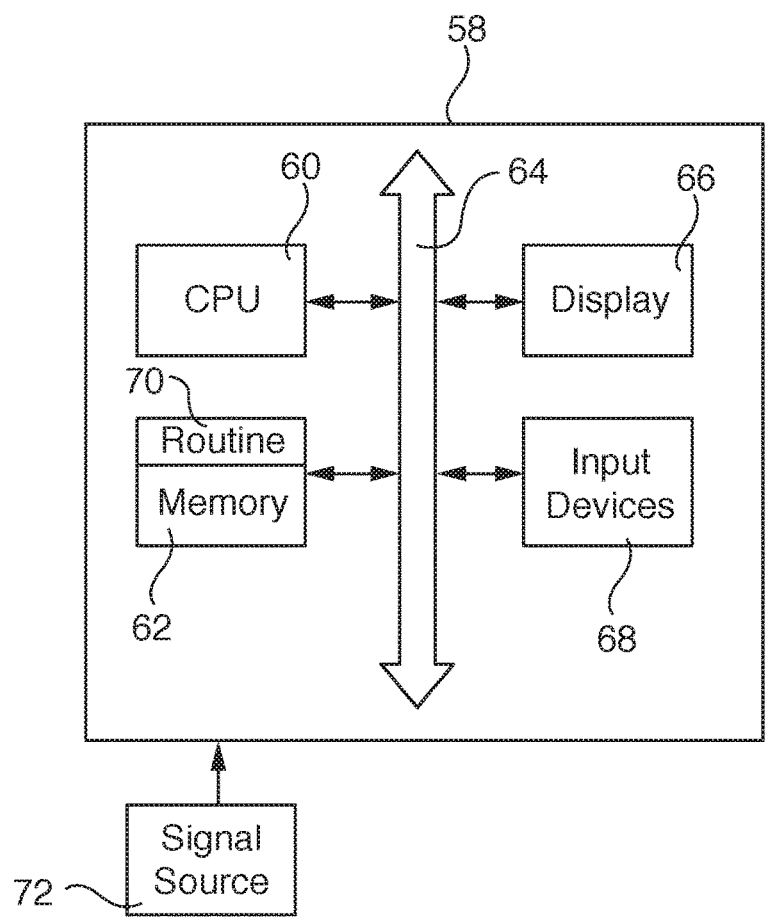
FIG. 3 is a block diagram of a computer system in which aspects of the above described invention may be implemented.

FIG. 3 is a block diagram of a computer system 58 in which aspects of the above described invention may be implemented. The computer system 58 can comprise, inter alia, a central processing unit (CPU) 60, a memory 62 and an input/output (I/O) interface 64. The computer system 58 is generally coupled through the I/O interface 64 to a display 66 and various input devices 68 such as a mouse, keyboard, touchscreen, camera and others. The support circuits can include circuits such as cache, power supplies, clock circuits, and a communications bus. The memory 62 can include random access memory (RAM), read only memory (ROM), disk drive, tape drive, storage device etc., or a combination thereof. In accordance with an aspect, the present invention can be implemented as a routine 70 that is stored in memory 62 and executed by the CPU 60 to process a signal from a signal source 72. As such, the computer system 58 is a general-purpose computer system that becomes a specific purpose computer system when executing the routine 70. The computer system 58 can communicate with one or more networks such as a local area network (LAN), a general wide area network (WAN), and/or a public network (e.g., the Internet) via a network adapter. In addition the computer system 58 may be used as a server as part of a cloud computing system where tasks may be performed by remote processing devices that are linked through a communications network. In a distributed cloud computing environment, program modules may be located in both local and remote computer system storage media including memory storage devices.

The computer system 58 also includes an operating system and micro-instruction code. The various processes and functions described herein may either be part of the micro-instruction code or part of the application program (or a combination thereof) that is executed via the operating system. In addition, various other peripheral devices may be connected to the computer platform such as an additional data storage device and a printing device. Examples of well-known computing systems, environments, and/or configurations that may be suitable for use with computer system 58 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices and the like.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A device for transmitting magnetic flux data generated by an electrical generator comprising:
   a flux probe carried by the generator to enable detection of a magnetic flux of the generator;
   a computing system comprising an interface and an analog-to-digital converter; and
   a calibration circuit in electrical communication with the flux probe by a first conductor and the interface by a second conductor wherein the calibration circuit measures a resistance of the second conductor and a voltage of the flux probe, and wherein a gain is calculated based on a conductor resistance of the second conductor and the voltage of the flux probe to provide an input voltage at the interface to transmit magnetic flux data to the computing system.

2. The device according to claim 1, wherein the gain is obtained from a gain look-up table derived from testing of a prototype device.

3. The device according to claim 1, wherein ends of the second conductor are shorted when measuring the conductor resistance of the second conductor and the flux probe voltage.

4. The device according to claim 1, further comprising a power source for energizing the device.

5. The device according to claim 4, wherein the power source is a battery.

6. A method comprising:
   measuring a flux probe voltage of a flux probe that detects a magnetic flux of an electrical generator via a calibration circuit, wherein the flux probe is in electrical communication with the calibration circuit by a first conductor and wherein the calibration circuit is in electrical communication with an interface of a computer system by a second conductor, wherein the computer system comprises an analog-digital converter;
   measuring a resistance of the second conductor via the calibration circuit; and
   determining a gain based on the flux probe voltage and a conductor resistance of the second conductor to provide an input voltage at the interface to transmit magnetic flux data to the computer system.

7. The method according to claim 6, wherein the gain is obtained from a gain look-up table derived from testing of a prototype device.

8. The method according to claim 6, further including shorting the ends of the second conductor when measuring the conductor resistance of the second conductor and the flux probe voltage.

9. The method according to claim 6, further including providing a power source for energizing the calibration circuit.

10. The method according to claim 9, wherein the power source is a battery.

11. A device for transmitting magnetic flux data generated by an electrical generator, comprising:
    a flux probe carried by the generator and adapted to detect a magnetic flux of the generator;
    a computing system comprising a first interface and an analog-to-digital converter;
    a calibration circuit in electrical communication with the flux probe by a first conductor and the first interface by a second conductor,
       wherein ends of the second conductor are shorted and the calibration circuit is adapted to measure a voltage of the flux probe and a resistance of the shorted second conductor, and
       wherein a gain is determined based on a conductor resistance of the and second conductor and the voltage of the flux probe to provide an input voltage at the first interface to transmit the magnetic flux data to the computing system; and
    a portable power source for energizing the device.

12. The device according to claim 11, wherein the gain is obtained from a gain look-up table derived from testing of a prototype device.

* * * * *